(12) United States Patent
Haddad et al.

(10) Patent No.: US 7,265,222 B2
(45) Date of Patent: Sep. 4, 2007

(54) PROCESS OF MAKING DI-ARYL UREA COMPOUNDS

(75) Inventors: Nizar Haddad, Danbury, CT (US); Xudong Wei, Ridgefield, CT (US); Chris Hugh Senanayake, Brookfield, CT (US); Jinghua Xu, Bethel, CT (US); Nathan Yee, Danbury, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 479 days.

(21) Appl. No.: 10/881,589

(22) Filed: Jun. 30, 2004

(65) Prior Publication Data

US 2004/0266767 A1 Dec. 30, 2004

Related U.S. Application Data

(60) Provisional application No. 60/483,720, filed on Jun. 30, 2003.

(51) Int. Cl.
*C07D 239/34* (2006.01)
(52) U.S. Cl. ........................... 544/320; 544/321
(58) Field of Classification Search ................ 544/320, 544/321
See application file for complete search history.

(56) References Cited

FOREIGN PATENT DOCUMENTS

| WO | WO 02/083628 A1 | 10/2002 |
|---|---|---|
| WO | WO 02/092576 A1 | 11/2002 |
| WO | WO 2004/014870 A1 | 2/2004 |

*Primary Examiner*—Deepak Rao
(74) *Attorney, Agent, or Firm*—Michael Morris; Mary-Ellen M. Devlin; Anthony P. Bottino

(57) ABSTRACT

Disclosed is a process of making compounds of formula(I):

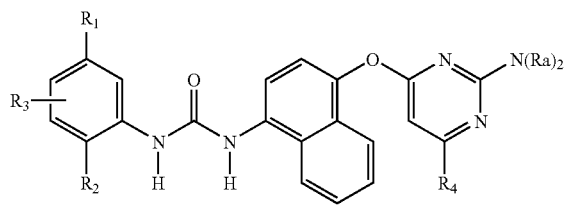

(I)

wherein $R_1$, $R_2$, $R_3$, $R_4$ and Ra of formula(I) are defined herein. The product compounds inhibit production of cytokines involved in inflammatory processes and are thus useful for treating diseases and pathological conditions involving inflammation. Also disclosed are intermediates useful in making such compounds.

8 Claims, No Drawings

PROCESS OF MAKING DI-ARYL UREA COMPOUNDS

APPLICATION DATA

This application claims benefit to U.S. provisional application Ser. No. 60/483,720 filed Jun. 30, 2003.

TECHNICAL FIELD OF THE INVENTION

This invention relates to a process of making di-aryl urea compounds of formula (I):

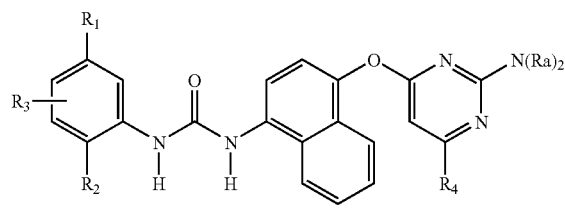

wherein $R_1$, $R_2$, $R_3$, X and W of formula(I) are defined below. The compounds inhibit production of cytokines involved in inflammatory processes and are thus useful for treating diseases and pathological conditions involving inflammation such as chronic inflammatory disease.

BACKGROUND OF THE INVENTION

Compounds which modulate release of one or more of the aforementioned inflammatory cytokines can be useful in treating diseases associated with release of these cytokines. For example, WO 98/52558 discloses heteroaryl urea compounds which are indicated to be useful in treating cytokine mediated diseases. WO 99/23091 discloses another class of urea compounds which are useful as anti-inflammatory agents. WO 99/32463 relates to aryl ureas and their use in treating cytokine diseases and proteolytic enzyme mediated disease. WO 00/41698 discloses aryl ureas said to be useful in treating p38 MAP kinase diseases.

Di-substituted aryl and heteroaryl compounds are also disclosed in U.S. Pat. Nos. 6,080,763; 6,319,921; 6,297,381, 6,358,945 and 6,492,393. The compounds in the patents are alleged to possess anti-cytokine activity and are therefore useful in treating diseases associated with inflammation.

U.S. provisional application No. 60/401,921, commonly owned by the assignee of the present application, relates to flourinated di-aryl urea compounds of formula(I):

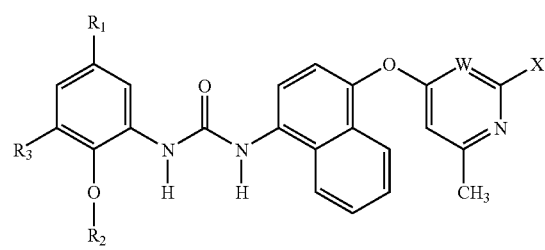

wherein $R_1$, $R_2$, $R_3$, X and W of formula(I) are defined therein. The compounds inhibit production of cytokines involved in inflammatory processes and are thus useful for treating diseases and pathological conditions involving inflammation. Also disclosed are processes for preparing compounds of the formula (I). The advantage provided by the present invention allows reducing the synthetic sequence to three steps and overcome low yields and exothermic conditions.

BRIEF SUMMARY OF THE INVENTION

It is therefore an object of the invention to provide a process of making di-aryl urea compounds of formula(I):

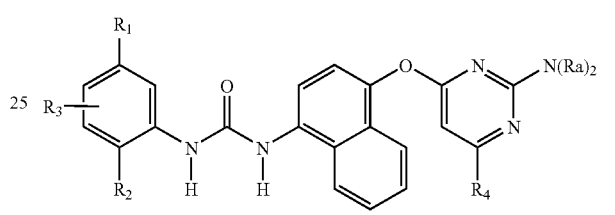

wherein $R_1$, $R_2$, $R_3$, $R_4$ and Ra of formula(I) are defined below; according to the following general scheme:

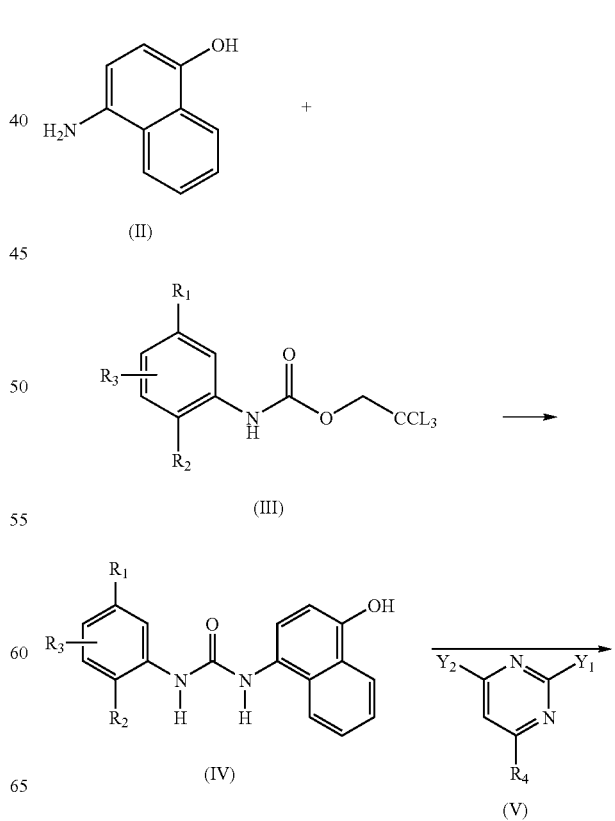

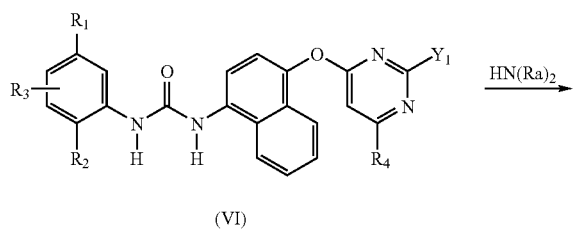

(VI)

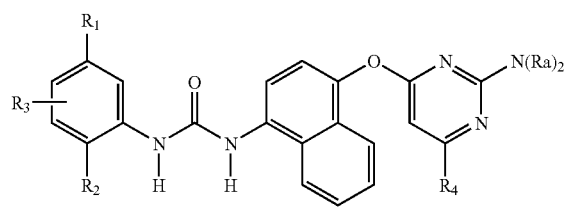

(I)

DETAILED DESCRIPTION OF THE INVENTION

In a generic aspect of the invention, there is provided a process of making compounds of the formula (I):

(I)

$R_1$ is C1-10 alkyl branched or unbranched or C3-10 cycloalkyl each optionally partially or full halogenated;

$R_2$ C1-10 alkyl branched or unbranched, C1-10 alkoxy branched or unbranched, C3-10 cycloalkyl each optionally partially or full halogenated and optionally substituted by aryl or $R_2$ is aryl;

$R_3$ is attached at the 3- or 4-position on the phenyl ring and is hydrogen, C1-10 alkyl, carbocycle, heterocycle, heteroaryl or $R_4$—S(O)$_2$—NH— wherein $R_4$ is chosen from $C_{1-5}$ alkyl or carbocycle;

$R_4$ is chosen from C1-5 alkyl or C1-5 alkoxy;

For N(Ra)$_2$, $R^a$ is independently chosen from hydrogen, C1-5 alkyl, aryl, arylC1-3 alkyl, C3-7cycloalkyl, C3-7cycloalkyl C1-3 alkyl, C1-5alkoxyC1-5alkyl and heterocyclyl C1-3 alkyl wherein the heterocycyl is chosen from tetrahydrofuran, pyrrolidinyl and morpholinyl, each $R^a$ where possible is optionally substituted by one to two C1-5 alkyl, C1-5 alkoxy or amino di-substituted by C1-5 alkyl;

said process comprising a) reacting an aryl amine (II) with a carbamate of the formula (III) in the presence of an aprotic solvent and an aprotic base at a temperature between 0° C. and 100° C. for a time of 1-24 hrs to produce the intermediate compound of the formula (IV):

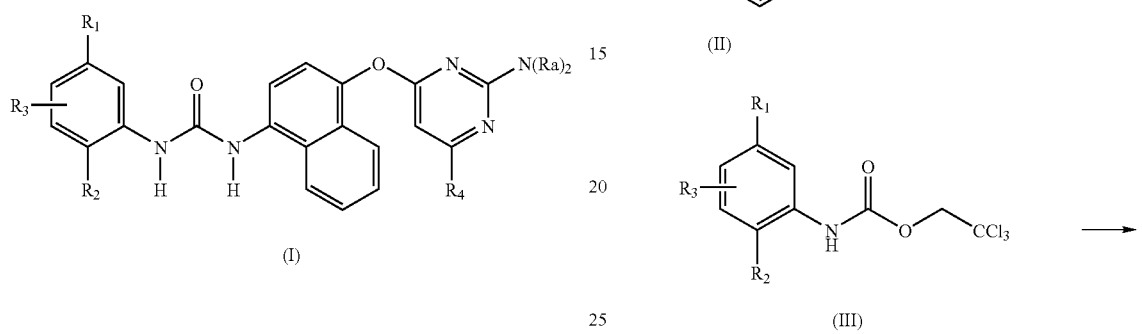

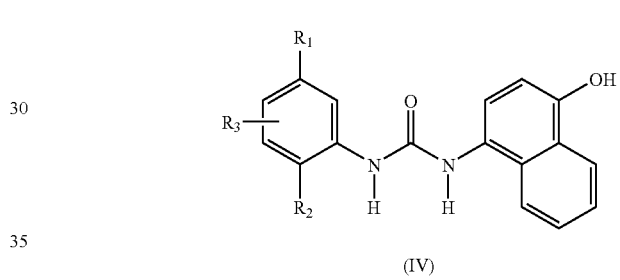

In this step, preferred solvents are NMP, DMSO, THF, EtOAc, Dioxane;

preferred aprotic bases are N-methylpyrrolidinone, N-methylpyrrolidine, triethylamine (preferably 1.35 eq), DMAP (preferably 0.2 eq);

preferred time 16 h; and a preferred temperature is about 45° C.

b) reacting intermediate compound of the formula (IV) with a compound of the formula (V) in the presence of polar solvent and a base at a temperature between 0° C. and 100° C. for a time of 1-24 hrs to produce the intermediate compound of the formula (VI):

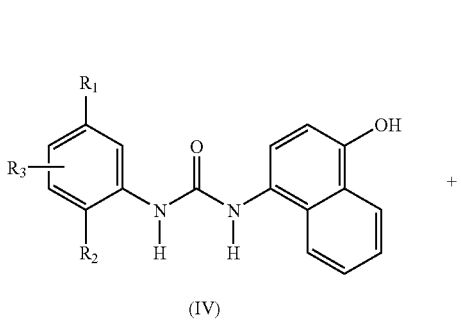

(IV)

where in the formula (V), $Y_1$ is halogen chosen from Cl, Br, I and F and $Y_2$ is halogen chosen from Cl and F. Preferably, $Y_1$ is Cl and $Y_2$ is Cl.

In this step, preferred solvents are C1-5 alcohol, preferably ethanol;
preferred aprotic bases are carbonates such as $Na_2CO_3$;
preferred time is 24 h; and
a preferred temperature is about 45° C.

c) reacting formula (VI) with a $HN(Ra)_2$ compound wherein Ra is as described above, in the presence of polar aprotic solvent and an aprotic base at a temperature between 0° C. and 100° C. for a time of 1-24 hrs to produce the compound of the formula (I), and subsequently isolating the product compound:

In this step, preferred solvents are Dioxane, Toluene, TGME, Triethylene glycol, preferably TGME (tri(ethylene glycol) monomethyl ether), KF;
preferred time is 18 h; and
a preferred temperature is about 60° C.

In another embodiment the invention provides a process of making compounds of the formula (I) as described immediately above and wherein
$R_1$ is —$CF_3$, —$CH(CH_3)(CF_3)$, —$CH(CF_3)_2$, —$OCF_3$, —$CF_2CF_3$;
$R_2$ is —O—$C_{1-5}$ alkyl;
$R_3$ is hydrogen or $R_4$—$S(O)_2$—NH— wherein $R_4$ is chosen from $C_{1-5}$ alkyl or carbocycle;
$R_4$ is chosen from C1-4 alkyl or C1-4 alkoxy.

In another embodiment the invention provides a process of making compounds of the formula (I) as described immediately above and wherein
$R_1$ is —$CF_3$, —$CH(CH_3)(CF_3)$, —$CH(CF_3)_2$, —$OCF_3$ or —$CF_2CF_3$;
$R_2$ is —O—$C_{1-3}$ alkyl;
For $N(Ra)_2$, $R^a$ is independently chosen from hydrogen, C1-5 alkyl, phenylC1-3 alkyl, C3-6cycloalkyl, C3-6cycloalkyl C1-3 alkyl, C1-3alkoxyC1-3alkyl and heterocyclyl C1-3 alkyl wherein the heterocycyl is chosen from tetrahydrofuran, pyrrolidinyl and morpholinyl, each $R^a$ where possible is optionally substituted by one to two C1-3 alkyl, C1-3 alkoxy or amino di-substituted by C1-2 alkyl;
$R_4$ is chosen from C1-3 alkyl or C1-3 alkoxy.

In another embodiment the invention provides a process of making compounds of the formula (I) as described immediately above and wherein
$R_1$ is —$CF_3$, —$CH(CH_3)(CF_3)$, —$CH(CF_3)_2$ or —$CF_2CF_3$;
$R_2$ is —O—$C_{1-2}$ alkyl;
$R_4$ is chosen from C1-2 alkyl or C1-2 alkoxy.

In another embodiment the invention provides a process of making compounds of the formula (I) as described immediately above and wherein
$R_1$ is —$CF_3$;
$R_2$ is —O—$CH_3$.
$R_4$ is methyl or methoxy.

In another embodiment the invention provides a process of making compounds of the formula (I) as described immediately above and wherein
$R_4$ is methyl;
$N(Ra)2$ is:
$NH_2$, $NH(CH_3)$, —$NHCH_2CH_2N(CH_3)_2$, —$NHCH_2CH_2$—O—$CH_3$, —NH—$CH_2$—$N(CH_3)_2$,—

Preferred intermediate compounds include:

-continued

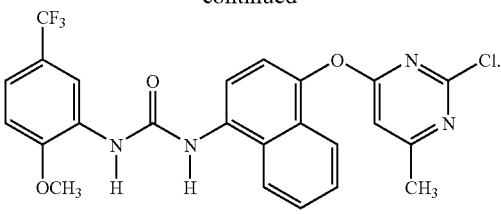

In all the compounds disclosed hereinabove in this application, in the event the nomenclature is in conflict with the structure, it shall be understood that the compound is defined by the structure.

All terms as used herein in this specification, unless otherwise stated, shall be understood in their ordinary meaning as known in the art. For example, "C1-3 alkoxy" is a C1-3(not an example used) alkyl with a terminal oxygen, such as methoxy, ethoxy, propoxy. All alkyl, alkenyl and alkynyl groups shall be understood as being branched or unbranched where structurally possible and unless otherwise specified. Other more specific definitions are as follows:

Carbocycles include hydrocarbon rings containing from three to ten carbon atoms. These carbocycles may be either aromatic and non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used inerchangeably.

The term "heterocycle" refers to a stable nonaromatic 4-8 membered (but preferably, 5 or 6 membered) monocyclic or nonaromatic 8-11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure. Unless otherwise stated, heterocycles include but are not limited to, for example oxetanyl, pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl, dithianyl or 2-oxa- or 2-thia-5-aza-bicyclo[2.2.1]heptanyl.

The term "heteroaryl" shall be understood to mean an aromatic 5-8 membered monocyclic or 8-11 membered bicyclic ring containing 1-4 heteroatoms such as N,O and S. Unless otherwise stated, such heteroaryls include: pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzooxazolonyl, benzo[1,4]oxazin-3-onyl, benzodioxolyl, benzo[1,3]dioxol-2-onyl, tetrahydrobenzopyranyl, indolyl, indolinyl, indolonyl, indolinonyl, phthalimidyl.

Each aryl or heterocycle unless otherwise specified includes it's partially hydrogenated derivative. For example, pyrrolidinyl may include pyrrolinyl, phenyl may include it's hydrogenated derivatives such as cyclohexenyl. Other partially or fully hydrogenated derivatives will be apparent to one of ordinary skill in the art.

In all alkyl groups or carbon chains one or more carbon atoms can be optionally replaced by heteroatoms: O, S or N. It shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in defintions such as but not limited to: alkoxycarbonyl, acyl, amido and thioxo.

As used herein, "nitrogen" and "sulfur" include any oxidized form of nitrogen and sulfur and the quaternized form of any basic nitrogen.

The term "halogen" as used in the present specification shall be understood to mean bromine, chlorine, fluorine or iodine, preferably fluorine. The definitions "partially or fully halogenated"; "substituted by one or more halogen atoms", includes for example, mono, di or tri halo derivatives on one or more carbon atoms. All alkyl, alkoxy, aryl moities shall be understood to be optionally halogenated unless otherwise indicated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

EXPERIMENTAL PROCEDURE

Step 1

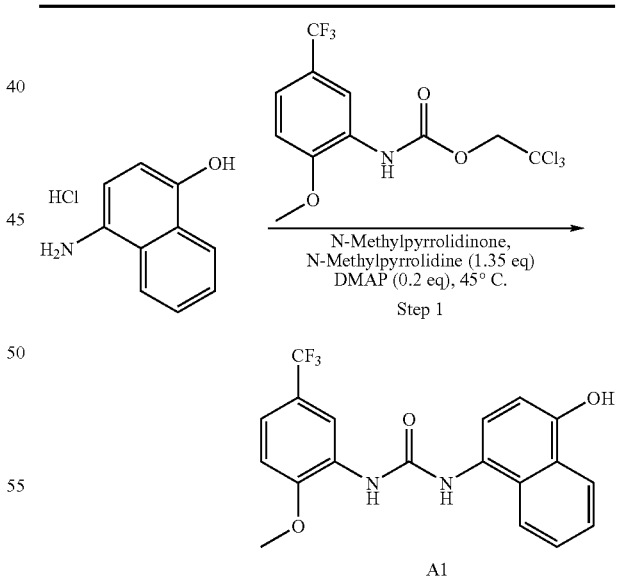

| Compound | MW | Mass | mol | Equivalent |
|---|---|---|---|---|
| 4-aminonaphthol hydrochloride | 195.65 | 4.70 g | 0.024 | 1.20 |
| Carbamate | 366.55 | 7.33 g | 0.020 | 1.00 |
| DMAP | 122.17 | 0.49 g | 0.004 | 0.20 |
| N-Methylpyrrolidine | 85.15 | 2.34 g | 0.027 | 1.35 |
| N-Methylpyrrolidinone | | 20 ml | | solvent |

4-Aminonaphthol hydrochloride, carbamate, DMAP and N-Methylpyrrolidine were dissolved in N-Methylpyrrolidinone. The reaction mixture was stirred at 45° C. for 2 days, HPLC indicated completion of reaction with 0.5% (area) remaining carbamate. Water (ca. 150 ml) and 1 N HCl (20 ml) were added. The resulting suspension was stirred for 10 h. The precipitate was filtered, washed with water and dried to give ca. 9.3 g of crude compound. Assay shows 7.1 g of product in it. Yield ca. 94.4%.

Step 2

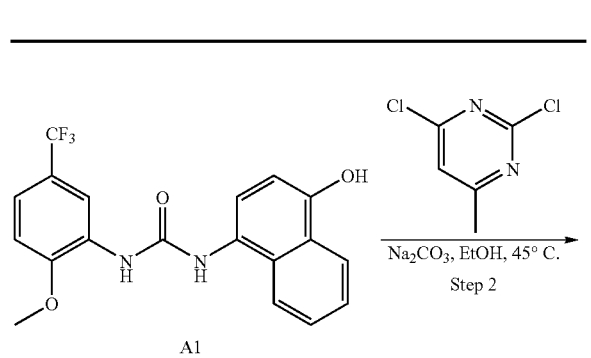

A1

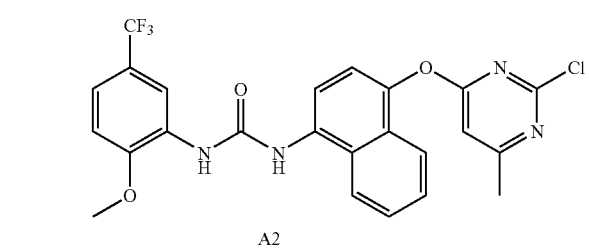

A2

| Compound | MW | amount | mol | Eq. |
|---|---|---|---|---|
| A1 | 376.3 | 200 g | 0.53 | 1 |
| Dichloropyrimidine | 163.0 | 95 g | 0.58 | 1.1 |
| Na$_2$CO$_3$ | 106 | 56.4 g | 0.53 | 1 |
| EtOH | | 1.0 L | | solvent |
| H$_2$O | | 0.15 L | | solvent |

To a 5 liter round bottom flask was added ArOH, dichloropyrimidine, Na$_2$CO$_3$ and solvent EtOH—H$_2$O. The reaction mixture was warmed to 45° C. and stirred for 1 day. The reaction was monitored by HPLC, when ArOH was detected below 0.5%, the reaction was cooled down to room temperature then filtered. The solid was washed with 400 mL EtOH:H$_2$O (80:20) and dried to give 230 g of of the product in 86% yield.

Part of the crude product (200 g) was washed with THF (700 mL) at 60° C. for 2 hours with stirring. After cooled down to 20° C., the solid was filtered and dried to give 165 g. 82% recovery. The isomer was reduced from 6% to 4.5% by NMR. This product was used for next step (step 3).

Step 3

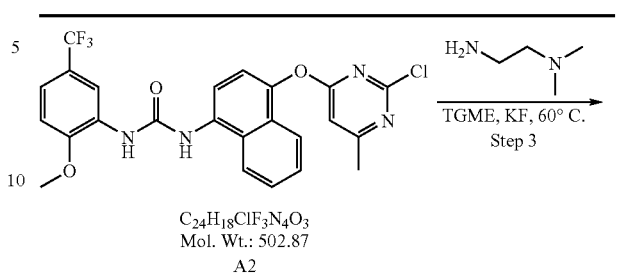

C$_{24}$H$_{18}$ClF$_3$N$_4$O$_3$
Mol. Wt.: 502.87
A2

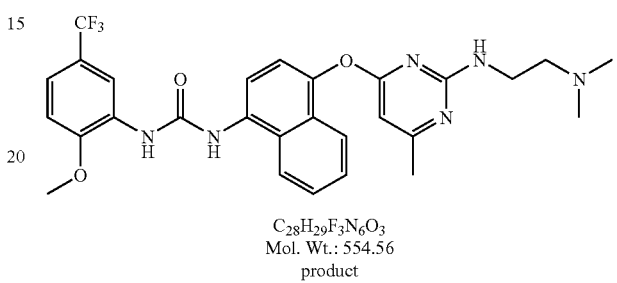

C$_{28}$H$_{29}$F$_3$N$_6$O$_3$
Mol. Wt.: 554.56
product

| Compound | MW | Mass | mol | Eq. |
|---|---|---|---|---|
| A2 | 502.87 | 165 g | 0.33 | 1 |
| Me$_2$NCH$_2$CH$_2$NH$_2$ | 88.15 | 123 g | 1.40 | 4.24 |
| KF | 58.10 | 20.3 g | 0.35 | 1.06 |
| TGME | | 1.2 L | | solvent |

To a 5 liter round bottom flask was added compound A2, KF, tri(ethylene glycol) monomethyl ether and N,N-dimethylethylenediamine. The reaction mixture was stirred at room temperature (temperature rose to ca. 30° C.) for 15 minutes and then heated to 60° C. for 5 hours. HPLC then indicated ArCl below 0.1%. The reaction mixture was cooled down to room temperature, water (3.6 liter) was added and the resulting suspension was stirred for 16 h. Filtration and brief drying gave crude compound ca. 240 g (151 g by assay, 83% assay yield). This crude product was swished with 450 mL of acetonitrile for 3 hours at room temperature. Filtration and drying gave 133.5 g (73% yield) of the desired product as off-white solid.

What is claimed is:
1. A process of making compounds of the formula (I):

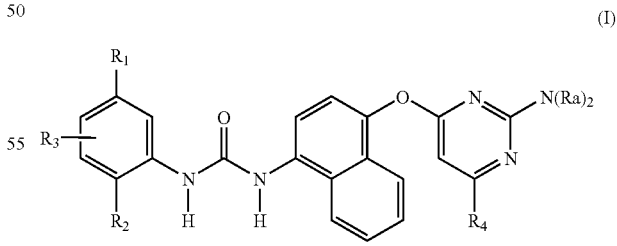

(I)

wherein:
R$_1$ is C1-10 alkyl branched or unbranched or C3-10 cycloalkyl each optionally partially or full halogenated;
R$_2$ C1-10 alkyl branched or unbranched, C1-10 alkoxy branched or unbranched, C3-10 cycloalkyl each optionally partially or full halogenated and optionally substituted by aryl or R$_2$ is aryl;

R3 is attached at the 3- or 4-position on the phenyl ring and is hydrogen, C1-10 alkyl, carbocycle, heterocycle, heteroaryl or R4—S(O)2—NH— wherein R4 is chosen from C1-5 alkyl or carbocycle;

R4 is chosen from C1-5 alkyl or C1-5 alkoxy;

for N(Ra)2, R^a is independently chosen from hydrogen, C1-5 alkyl, aryl, arylC1-3 alkyl, C3-7cycloalkyl, C3-7cycloalkyl C1-3 alkyl, C1-5alkoxyC1-5alkyl and heterocyclyl C1-3 alkyl wherein the heterocycyl is chosen from tetrahydrofuran, pyrrolidinyl and morpholinyl, each R^a where possible is optionally substituted by one to two C1-5 alkyl, C1-5 alkoxy or amino di-substituted by C1-5 alkyl;

said process comprising a) reacting an aryl amine (II) with a carbamate of the formula (III) in the presence of an aprotic solvent and an aprotic base at a temperature between 0° C. and 100° C. for a time of 1-24 hrs to produce the intermediate compound of the formula (IV):

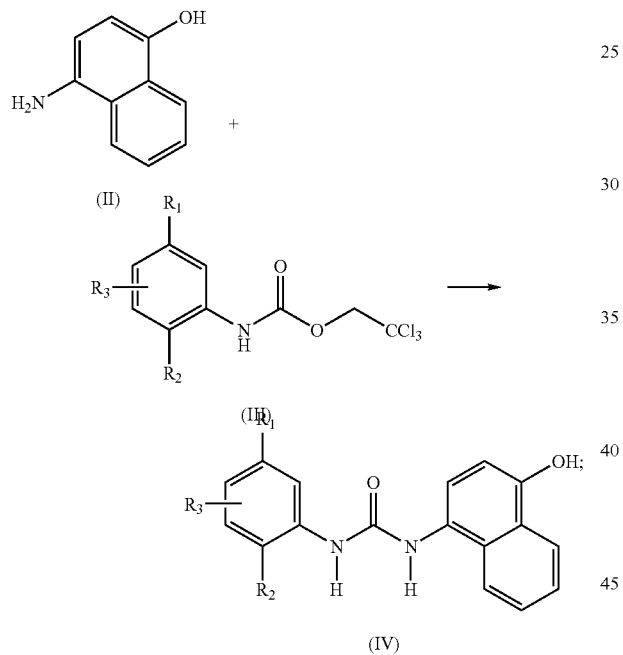

b) reacting intermediate compound of the formula (IV) with a compound of the formula (V) in the presence of polar solvent and an aprotic base at a temperature between 0° C. and 100° C. for a time of 1-24 hrs to produce the intermediate compound of the formula (VI):

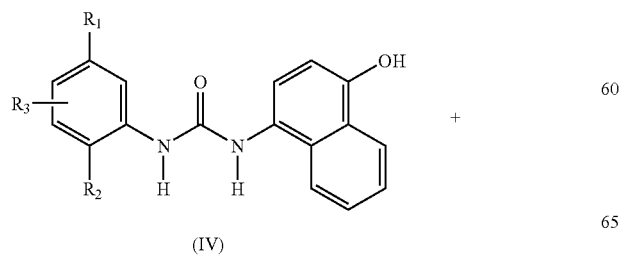

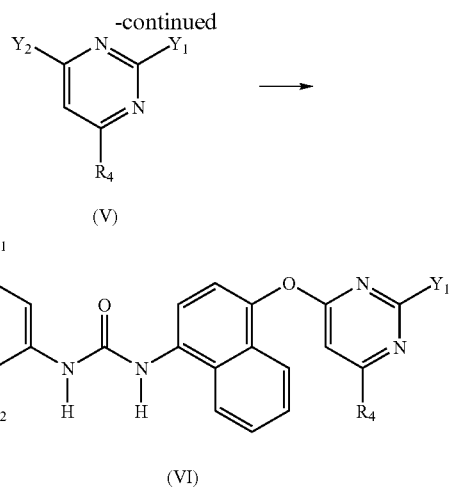

where in the formula (V), $Y_1$ is halogen chosen from Cl, Br, I and F and $Y_2$ is halogen chosen from Cl and F;

c) reacting formula (VI) with a HN(Ra)2 compound wherein Ra is as described above, in the presence of polar aprotic solvent and an aprotic base at a temperature between 0° C. and 100° C. for a time of 1-24 hrs to produce the compound of the formula (I), and subsequently isolating the product compound:

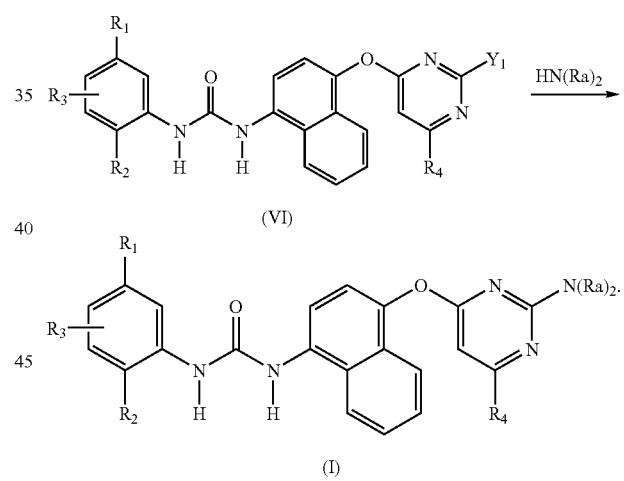

2. The process according to claim 1 and wherein:

in step a)

the aprotic solvent is chosen from NMP, DMSO, THF, EtOAc and Dioxane;

the aprotic base is chosen from N-methylpyrrolidinone, N-methylpyrrolidine, triethylamine and DMAP;

the time about 16 h; and the temperature is about 45° C.;

in step b)

$Y_1$ is Cl and $Y_2$ is Cl;

the polar solvent is a C1-5 alcohol;

the aprotic base is a carbonate;

the time is about 24 h; and the temperature is about 45° C.;

in step c)
the polar aprotic solvent is chosen from Dioxane, Toluene, TGME and Triethylene glycol with KF;
time is 18 h; and
temperature is about 60° C.

3. The process according to claim 2 and wherein:
in step a)
the aprotic solvent is chosen from NMP, DMSO, THF, EtOAc and Dioxane;
the aprotic base is chosen from N-methylpyrrolidinone, N-methylpyrrolidine, triethylamine and DMAP, wherein triethylamine is in an amount of about 1.35 eq and DMAP is in an amount of about 0.2 eq;
in step b)
$Y_1$ is Cl and $Y_2$ is Cl;
the polar solvent is ethanol;
the carbonate is $Na_2CO_3$;
in step c)
the polar aprotic solvent is TGME with KF.

4. The process according to claim 1 and wherein
$R_1$ is —$CF_3$, —$CH(CH_3)(CF_3)$, —$CH(CF_3)_2$, —$OCF_3$ or —$CF_2CF_3$;
$R_2$ is —O—$C_{1-5}$ alkyl;
$R_3$ is hydrogen or $R_4$—$S(O)_2$—NH— wherein $R_4$ is chosen from $C_{1-5}$ alkyl or carbocycle;
$R_4$ is chosen from C1-4 alkyl or C1-4 alkoxy.

5. The process according to claim 4 and wherein:
$R_2$ is —O—$C_{1-3}$ alkyl;
for $N(Ra)_2$, $R^a$ is independently chosen from hydrogen, C1-5 alkyl, phenylC1-3 alkyl, C3-6cycloalkyl, C3-6cycloalkyl C1-3 alkyl, C1-3alkoxyC1-3alkyl and heterocyclyl C1-3 alkyl wherein the heterocycyl is chosen from tetrahydrofuran, pyrrolidinyl and morpholinyl, each $R^a$ where possible is optionally substituted by one to two C1-3 alkyl, C1-3 alkoxy or amino di-substituted by C1-2 alkyl;
$R_4$ is chosen from C1-3 alkyl or C1-3 alkoxy.

6. The process according to claim 5 and wherein:
$R_1$ is —$CF_3$, —$CH(CH_3)(CF_3)$, —$CH(CF_3)_2$ or —$CF_2CF_3$;
$R_2$ is —O—$C_{1-2}$ alkyl;
$R_4$ is chosen from C1-2 alkyl or C1-2 alkoxy.

7. The process according to claim 6 and wherein:
$R_1$ is —$CF_3$;
$R_2$ is —O—$CH_3$;
$R_4$ is methyl or methoxy.

8. The process according to claim 7 and wherein:
$R_4$ is methyl;
$N(Ra)2$ is:
$NH_2$, $NH(CH_3)$, —$NHCH_2CH_2N(CH_3)_2$, —$NHCH_2CH_2$—O—$CH_3$, —NH—$CH_2$—$N(CH_3)_2$,

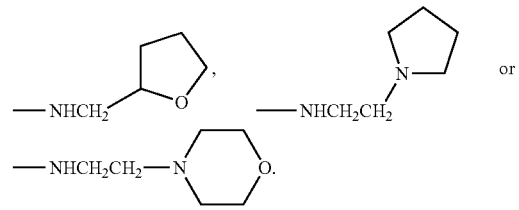

* * * * *